(12) United States Patent
Im et al.

(10) Patent No.: US 11,191,865 B2
(45) Date of Patent: Dec. 7, 2021

(54) MEDICAL FIBROUS STRUCTURE COMPRISING CALCIUM CARBOXYMETHYL CELLULOSE AND CHITOSAN COMPOUND AND PROCESS FOR PREPARING THE SAME

(71) Applicant: KOREA INSTITUTE OF INDUSTRIAL TECHNOLOGY, Cheonan-si (KR)

(72) Inventors: Jung Nam Im, Suwon-si (KR); Song Jun Doh, Suwon-si (KR); Tae Hee Kim, Suwon-si (KR); Yoonjin Kim, Yongin-si (KR); Chaehwa Kim, Seoul (KR); Gyu Dong Lee, Ansan-si (KR); Gahee Kim, Suwon-si (KR)

(73) Assignee: KOREA INSTITUTE OF INDUSTRIAL TECHNOLOGY, Chungcheongnam-do (KR)

( * ) Notice: Subject to any disclaimer, the term of this patent is extended or adjusted under 35 U.S.C. 154(b) by 113 days.

(21) Appl. No.: 15/736,758

(22) PCT Filed: Jun. 24, 2016

(86) PCT No.: PCT/KR2016/006807
§ 371 (c)(1),
(2) Date: Dec. 14, 2017

(87) PCT Pub. No.: WO2016/209048
PCT Pub. Date: Dec. 29, 2016

(65) Prior Publication Data
US 2018/0169291 A1   Jun. 21, 2018

(30) Foreign Application Priority Data
Jun. 26, 2015   (KR) .................. 10-2015-0091523

(51) Int. Cl.
| | |
|---|---|
| A61L 15/22 | (2006.01) |
| A61L 15/28 | (2006.01) |
| A61L 31/04 | (2006.01) |
| A61L 15/44 | (2006.01) |
| D04H 1/04 | (2012.01) |
| D04H 1/72 | (2012.01) |
| D06N 3/00 | (2006.01) |
| D06N 3/12 | (2006.01) |

(52) U.S. Cl.
CPC .............. *A61L 15/225* (2013.01); *A61L 15/22* (2013.01); *A61L 15/28* (2013.01); *A61L 15/44* (2013.01); *A61L 31/04* (2013.01); *D04H 1/04* (2013.01); *D04H 1/72* (2013.01); *D06N 3/0011* (2013.01); *D06N 3/0077* (2013.01); *D06N 3/0093* (2013.01); *D06N 3/12* (2013.01); *A61L 2300/418* (2013.01); *A61L 2400/04* (2013.01); *A61L 2420/02* (2013.01); *D06N 2201/042* (2013.01); *D06N 2203/024* (2013.01); *D06N 2205/10* (2013.01); *D06N 2207/04* (2013.01); *D06N 2211/00* (2013.01); *D10B 2201/22* (2013.01); *D10B 2509/022* (2013.01)

(58) Field of Classification Search
None
See application file for complete search history.

(56) References Cited

U.S. PATENT DOCUMENTS

| | | | |
|---|---|---|---|
| 2004/0243041 A1* | 12/2004 | Qin | .................. A61F 13/0243 602/41 |
| 2007/0160543 A1 | 7/2007 | Moller | |
| 2011/0021964 A1 | 1/2011 | Larsen et al. | |
| 2013/0012857 A1* | 1/2013 | Flynn | ............... A61F 13/00012 602/43 |
| 2013/0273235 A1* | 10/2013 | Huang | .................. A61L 15/28 427/2.31 |

FOREIGN PATENT DOCUMENTS

| | | |
|---|---|---|
| CN | 1921896 A | 2/2007 |
| CN | 102137684 A | 7/2011 |
| CS | 238016 B1 | 11/1985 |
| EP | 2695622 A1 | 2/2014 |
| JP | 2008038293 A | 2/2008 |
| JP | 5569398 B2 | 8/2014 |
| KR | 1020090110379 A | 10/2009 |
| KR | 1020110074006 A | 6/2011 |
| KR | 101355678 B1 | 1/2014 |
| WO | 9613282 A1 | 5/1996 |
| WO | 2013/079469 A1 | 6/2013 |

OTHER PUBLICATIONS

International Search Report dated Sep. 26, 2016 for PCT/KR2016/006807.
Chinese Office Action for CN Application No. 201680037541.9 dated Mar. 25, 2020.
Chinese Office Action for CN Application No. 201680037541.9 dated Jan. 19, 2021.

* cited by examiner

*Primary Examiner* — Robert A Wax
*Assistant Examiner* — Randeep Singh
(74) *Attorney, Agent, or Firm* — Cantor Colburn LLP

(57) ABSTRACT

Disclosed are a medical fiberous structure and a method for preparing the same, wherein the medical fiberous structure comprises calcium carboxymethyl cellulose and a chitosan compound, at least one of the calcium carboxymethyl cellulose and the chitosan compound having a fibrous shape.

12 Claims, 10 Drawing Sheets

| | Absorption time | Before absorption | After absorption |
|---|---|---|---|
| Example 2 | < 1 second |  |  |
| Example 4 | <1 second |  |  |
| Example 5 | <1 second |  |  |
| Example 6 | <1 second |  |  |
| Comparative example 3 | >10 minutes |  |  |
| Comparative example 4 | <1 second |  |  |
| Comparative example 5 | >10 minutes |  |  |
| Comparative example 6 | <1 second |  |  |

MEDICAL FIBROUS STRUCTURE COMPRISING CALCIUM CARBOXYMETHYL CELLULOSE AND CHITOSAN COMPOUND AND PROCESS FOR PREPARING THE SAME

TECHNICAL FIELD

The present disclosure relates to a medical fibrous structure comprising calcium carboxymethyl cellulose and a chitosan compound and a process for preparing the same, and more particularly, to a fibrous structure with outstanding blood absorption capacity and improved blood coagulation properties and a process for preparing the same.

The present application claims priority to Korean Patent Application No. 10-2015-0091523 filed in the Republic of Korea on Jun. 26, 2015, the disclosure of which is incorporated herein by reference.

BACKGROUND ART

In various environments, animals including humans may be injured. This injury often accompanies bleeding. In some cases, injuries and bleeding are not dangerous, and bleeding stops by general blood coagulation activities with no outside help. Unfortunately, in other cases, a considerable amount of bleeding may occur.

Particularly, excessive bleeding endangers human life in an instant and is one of the main leading causes of death, and there are reports that the number of deaths from excessive bleeding in U.S. is over 50,000 each year. The immediate and effective stopping of bleeding can greatly increase the probability of survival, so the use of hemostatic agents in the battlefield, real-life emergency situations, and operating rooms is very necessary.

Humans have devoted themselves for a long time to develop hemostatic agents to stop bleeding quickly, and various formulations for managing bleeding and skin damage occurred by many causes have been developed.

General gauzes or bandages have a hemostatic effect for light bleeding, but their application has limitation in life threatening severe bleeding, and chitosan, oxidized cellulose-based, or sodium carboxymethyl cellulose hemostatic agents have disadvantages because they have somewhat poor blood coagulation capability and adhesion to wound.

Current available hemostatic bandages such as collagen wound dressings or dry fibrin or thrombin wound dressings are in limited use for surgical applications, and in particular, in the case of a quick flow of blood such as hemorrhage, they are easily dissolved, which becomes limitation in use. These current available surgical hemostatic bandages are weak and thus are prone to damage caused by bending or loading due to the pressure.

Moreover, collagen-based hemostatic agents are high priced, significantly vary in properties from product to product, and are bad at keeping, and thrombin- and fibrinogen-containing hemostatic agents have problems with infection risk and hypersensitive reactions during treatment.

Additionally, inorganic-based hemostatic agents such as zeolite have been studied for procoagulation in blood, but it was reported that the use of activated zeolite for blood coagulation causes undesirable fever. Inorganic-based hemostatic products with no accompanying fever have been developed, but their blood coagulation capability is not yet good enough to apply to excessive bleeding.

Now, therefore, there are still the need for development of hemostatic agents having improved, better blood coagulation properties and hemostatic effect than earlier hemostatic agents that have been studied.

DISCLOSURE

Technical Problem

The present disclosure is directed to providing a medical fibrous structure with outstanding blood absorption capacity and rapid blood coagulation.

The present disclosure is further directed to providing a process for preparing the medical fibrous structure.

Technical Solution

To achieve the above object, according to an aspect of the present disclosure, there is provided a medical fibrous structure including calcium carboxymethyl cellulose, and a chitosan compound, wherein at least one of the calcium carboxymethyl cellulose and the chitosan compound is in fibrous form.

The medical fibrous structure may include at least one of a nonwoven fabric, a woven fabric, a knitted fabric, and a microfibril structure.

Both the calcium carboxymethyl cellulose and the chitosan compound may be in fibrous form.

The medical fibrous structure may include a substrate including fibers formed of at least one of calcium carboxymethyl cellulose and a chitosan compound, and a fiber layer disposed on at least one of at least one surface of the substrate and an inside of the substrate, the fiber layer including fibers formed of at least one of calcium carboxymethyl cellulose and a chitosan compound, and the substrate may be a nonwoven fabric, a woven fabric, or a knitted fabric.

The medical fibrous structure may be a microfibril structure including calcium carboxymethyl cellulose microfibrils and chitosan compound microfibrils.

One of the calcium carboxymethyl cellulose and the chitosan compound may be in fibrous form, and the other may be in powder form.

The medical fibrous structure may include a substrate including fibers formed of at least one of calcium carboxymethyl cellulose and a chitosan compound, and a coating layer disposed on at least one of at least one surface of the substrate and an inside of the substrate, the coating layer including powder formed of at least one of calcium carboxymethyl cellulose and a chitosan compound, and the substrate may be a nonwoven fabric, a woven fabric, or a knitted fabric.

The coating layer may be formed as a patterned layer on at least one surface of the nonwoven fabric.

The medical fibrous structure may be a microfibril structure including microfibrils formed of at least one of calcium carboxymethyl cellulose and a chitosan compound, and powder formed of at least one of calcium carboxymethyl cellulose and a chitosan compound.

The chitosan compound may be at least one of chitosan or chitosan derivatives.

The medical fibrous structure may further include a structure reinforcement on at least one of at least one surface and an inside of the medical fibrous structure.

According to another aspect of the present disclosure, there is provided a process for preparing a medical fibrous structure, the medical fibrous structure including calcium carboxymethyl cellulose and a chitosan compound, wherein at least one of the calcium carboxymethyl cellulose and the chitosan compound is in fibrous form.

The process may include preparing a nonwoven fabric, a woven fabric, or a knitted fabric including calcium carboxymethyl cellulose fibers and chitosan compound fibers.

The preparing of a nonwoven fabric may include mixing the calcium carboxymethyl cellulose fibers and the chitosan compound fibers to prepare a mixture, adding a dispersion medium, a medium for dispersion during wet-laid nonwoven process, to the mixture and blending them, and removing the dispersion medium.

The process may include preparing a substrate including fibers formed of at least one of calcium carboxymethyl cellulose and a chitosan compound, and forming a fiber layer including fibers formed of at least one of calcium carboxymethyl cellulose and a chitosan compound on at least one of at least one surface of the substrate and an inside of the substrate, and the substrate may be a nonwoven fabric, a woven fabric, or a knitted fabric.

The process may include adding a dispersion medium dispersion medium to fibers formed of at least one of the calcium carboxymethyl cellulose and the chitosan compound and blending them, removing the dispersion medium to prepare a nonwoven fabric, and forming a fiber layer including fibers formed of at least one of the calcium carboxymethyl cellulose and the chitosan compound on at least one of at least one surface of the nonwoven fabric and an inside of the nonwoven fabric.

The process may include preparing a microfibril structure including calcium carboxymethyl cellulose microfibrils and chitosan compound microfibrils.

The process may include preparing a substrate including fibers formed of at least one of calcium carboxymethyl cellulose and a chitosan compound, and forming a coating layer including powder formed of at least one of calcium carboxymethyl cellulose and a chitosan compound on at least one of at least one surface of the substrate and an inside of the substrate, and the substrate may be a nonwoven fabric, a woven fabric, or a knitted fabric.

The process may include adding a dispersion medium to fibers formed of at least one of the calcium carboxymethyl cellulose and the chitosan compound and blending them, removing the dispersion medium to prepare a nonwoven fabric, and forming a coating layer including powder formed of at least one of the calcium carboxymethyl cellulose and the chitosan compound on at least one of at least one surface of the nonwoven fabric and an inside of the nonwoven fabric.

The coating layer may be formed as a patterned layer.

The forming of a coating layer may include stacking the powder on the at least one surface of the nonwoven fabric and the inside of the nonwoven fabric, and applying water vapor to the powder-stacked nonwoven fabric to bind the powder and the nonwoven fabric.

The process may include adding a dispersion medium to fibers formed of at least one of the calcium carboxymethyl cellulose and the chitosan compound and powder formed of at least one of the calcium carboxymethyl cellulose and the chitosan compound and blending them, and removing the dispersion medium to prepare a nonwoven fabric.

The process may include preparing a microfibril structure including microfibrils formed of at least one of calcium carboxymethyl cellulose and a chitosan compound, and powder formed of at least one of calcium carboxymethyl cellulose and a chitosan compound.

The process may further include adding a structure reinforcement when preparing the medical fibrous structure, or combining the medical fibrous structure with a structure reinforcement.

Advantageous Effects

The medical fibrous structure according to an embodiment of the present disclosure has a superior hemostatic effect of the chitosan compound, and the outstanding fluid absorption and retention and a thickening effect of the calcium carboxymethyl cellulose and a blood-coagulation promoting function by calcium ions at the same time. The medical fibrous structure, thus, solves the conventional problems, such as somewhat slow absorption rate of chitosan, poor hemostatic efficiency and shape instability after gelation of sodium carboxymethyl cellulose fibers, and provides a synergistic effect of the superior fluid absorption properties and hemostatic effect.

Furthermore, as the medical fibrous structure according to an embodiment of the present disclosure includes a calcium carboxymethyl cellulose material in which divalent calcium ions are bonded with carboxyl groups of carboxymethyl cellulose, crosslinking between carboxymethyl cellulose molecular chains is induced, reducing a gel blocking phenomenon, resulting in markedly improved rate of fluid absorption, and calcium ions are released when contacted with blood or body fluid, promoting blood coagulation, resulting in further enhanced hemostatic performance.

The medical fibrous structure according to an embodiment of the present disclosure can be used as a variety of medical materials including hemostatic agents, adhesion prevention barriers, and wound dressings.

DESCRIPTION OF THE DRAWINGS

The accompanying drawings illustrate preferred embodiments of the present disclosure and, together with the foregoing disclosure, serve to provide further understanding of the technical spirit of the present disclosure. However, the present disclosure is not to be construed as being limited to the drawings.

MODE FOR CARRYING OUT THE INVENTION

Figure 1A:
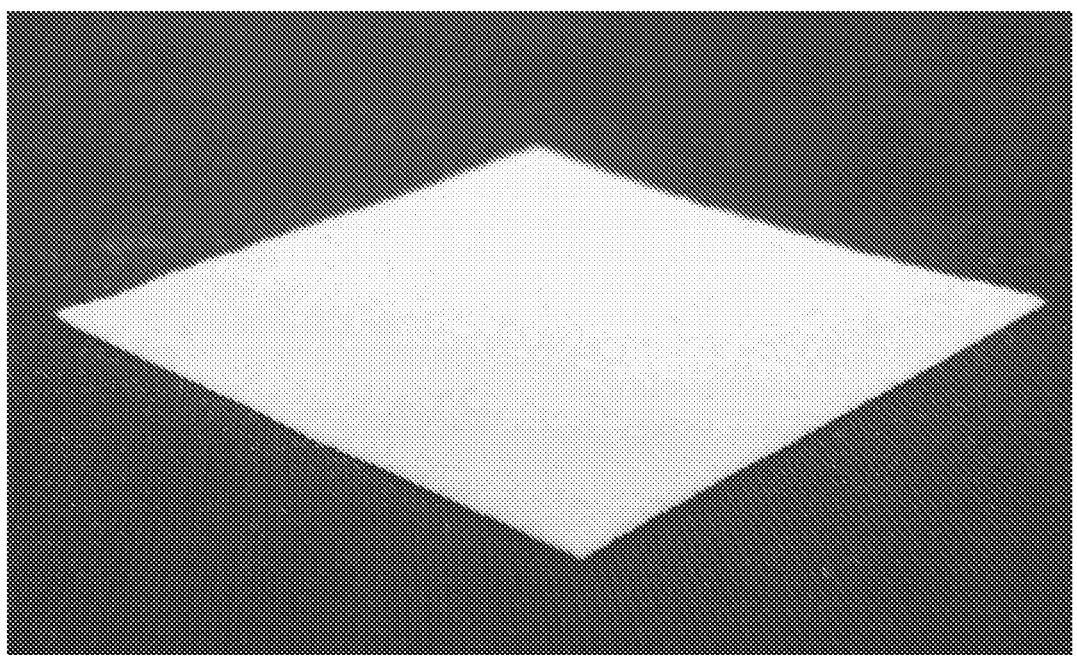
FIG. 1a is an optical photographic image of a medical fibrous structure prepared in example 1.

Hereinafter, the present disclosure will be described in detail. Prior to the description, it should be understood that the terms or words used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation.

Therefore, the disclosure described in the embodiment or example herein are just one most preferred embodiment or example of the present disclosure, not intended to represent all the technical aspects of the present disclosure, so it should be understood that alternatives, other equivalents and variations would be made thereto at the time the present application is filed.

A medical fibrous structure according to an aspect of the present disclosure includes calcium carboxymethyl cellulose and a chitosan compound, wherein at least one of the calcium carboxymethyl cellulose and the chitosan compound is in fibrous form.

In the medical fibrous structure, at least one of the calcium carboxymethyl cellulose and the chitosan compound is in fibrous form, i.e., in fibrous shape.

Furthermore, the medical fibrous structure may be in the shape of a nonwoven fabric, a woven fabric, a knitted fabric, a microfibril structure, or mixtures thereof.

Specifically, the medical fibrous structure may be in the shape of a nonwoven fabric, a woven fabric, a knitted fabric, a microfibril structure and mixtures thereof, formed of fibers alone or fibers and powder, preferably a knitted fabric or a nonwoven fabric, and more preferably a nonwoven fabric. In the case where the shape of the medical fibrous structure is of a nonwoven fabric, a preparing process is simple, control of pore properties is easy, and fluid absorption properties can be further improved.

The fibrous form, fibrous shape, or fiber as used herein refers to a group of linear materials that are long and thin and can be flexibly bent due to low bending resistance, and such a fiber can be classified, according to its length, into a microfibril having a length of 1 mm or less, a short fiber (short cut fiber) for wet-laid nonwoven fabrics cut to 0.1 to 40 mm, a short fiber (staple fiber) for dry-laid nonwoven fabrics having a length of 10 to 130 mm, and a continuous fiber (long fiber, filament) for woven fabrics and knitted fabrics.

The nonwoven fabric as used herein refers to a type of fibrous structure obtained by arranging fibers in a parallel or random direction without undergoing a weaving process, and bonding them through mechanical entanglement between fibers, addition of a resin adhesive, heat fusion, or formation of a chemical complex.

The nonwoven fabric may be manufactured by various processes including wet-lay (also known as immersion or paper-making), dry-lay, spunlace, and electrospinning.

Among them, the dry-laid nonwoven fabric includes a chemical bonding nonwoven fabric manufactured by allowing an adhesive to penetrate into fibers, followed by a drying process, a thermal bonding nonwoven fabric manufactured by mixing fibers having plasticity of low melting point and fusing or melting by heat or pressure to bind fiber tissues, an air lay nonwoven fabric manufactured using compressed air and an adhesive, and a needle punching nonwoven fabric manufactured by mechanically bonding fibers through a web using a special needle, and is desirable in terms of improvements in the tensile strength or shape stability of the nonwoven fabric. Furthermore, the wet-laid nonwoven fabric may be manufactured by the same process as a papermaking method, but raw material is not limited to only pulps and various types of fibers are used, and after dispersing such fibers in a dispersion medium, i.e., a solution for dispersion, the dispersion medium is removed through a wire or screen for paper-making and the fibers are dried to manufacture a nonwoven fabric, and it is desirable in terms of evenness improvement and an advantage is the use of short fibers having a shorter length, such as microfibrils, compared to a dry-laid process.

Furthermore, the woven fabric as used herein refers to a fibrous structure made of fibers that are divided into warp and weft, the weft passing across the warp, and the knitted fabric as used herein refers to a fibrous structure formed from a continuous loop of fiber, and they may be manufactured by a variety of methods that can be used in the art.

The microfibril structure as used herein refers to a fibrous structure formed by gathering microfibrils without a special shape, or mixing microfibrils with powder. The length of the microfibril may be, for example, 1 mm or less, or from 0.05 to 0.5 mm.

Furthermore, the inside of the substrate, the nonwoven fabric, or the medical fibrous structure as used herein refers to a space formed by fibers included in the substrate, the nonwoven fabric, or the medical fibrous structure, namely, a space formed between adjacent or entangled fibers.

According to an embodiment of the present disclosure, both the calcium carboxymethyl cellulose and the chitosan compound may be in fibrous form, and in this case, the medical fibrous structure may be at least one of a nonwoven fabric, a woven fabric, and a knitted fabric, including calcium carboxymethyl cellulose fibers and chitosan compound fibers.

For example, the medical fibrous structure may include a substrate including fibers formed of at least one of calcium carboxymethyl cellulose and a chitosan compound; and a fiber layer disposed on at least one of at least one surface of the substrate and an inside of the substrate, wherein the fiber layer includes fibers formed of at least one of calcium carboxymethyl cellulose and a chitosan compound.

That is, the substrate may include calcium carboxymethyl cellulose fibers alone, chitosan compound fibers alone, or mixtures thereof, and may have a fiber layer disposed on at least one of one surface, two surfaces, and an inside of the substrate, and the fiber layer may also include calcium carboxymethyl cellulose fibers alone, chitosan compound fibers alone, or mixtures thereof.

In this instance, the substrate may be a nonwoven fabric, a woven fabric, or a knitted fabric manufactured using calcium carboxymethyl cellulose fibers alone, chitosan compound fibers alone, or mixtures thereof.

Furthermore, optionally, in addition to these fibers, the substrate may further include various types of natural or artificial fibers or powder within the applicable scope for medical use.

According to an embodiment of the present disclosure, the medical fibrous structure may be a microfibril structure including calcium carboxymethyl cellulose microfibrils and chitosan compound microfibrils.

Here, the calcium carboxymethyl cellulose microfibril and the chitosan compound microfibril as used herein refer to a microfibril having a fiber length of 1 mm or less in the carboxymethyl cellulose fibers and chitosan compound fibers as described in the foregoing.

The microfibril structure as used herein refers to microfibrils that are gathered without a special shape and mechanically entangled. Furthermore, the microfibril structure may be applied in the manner of putting on cotton tufty, particulate, powdery, and a gauze-like fiber reinforcement in various sizes at a wound site. Particularly, to easily remove after hemostasis treatment is completed, components used in the microfibril structure, such as microfibrils, may be dissolved when contacted with a saline solution, body fluid, or blood.

According to an embodiment of the present disclosure, one of the calcium carboxymethyl cellulose and the chitosan compound may be in fibrous form, and the other may be in powder form.

The powder form as used herein refers to powder or flour collectively consisting of finely pulverized grains, and may be classified into granular, coarse, fine, and ultrafine powder according to its size, and for example, may have an average particle diameter of from 1 to 1,000□, from 10 to 1,000□, or from 100 to 1,000□.

For example, the medical fibrous structure may include a substrate including fibers formed of at least one of calcium carboxymethyl cellulose and a chitosan compound; and a coating layer disposed on at least one of at least one surface of the substrate and an inside of the substrate, wherein the coating layer includes powder formed of at least one of calcium carboxymethyl cellulose and a chitosan compound.

In this instance, as described in the foregoing, the substrate may be a nonwoven fabric, a woven fabric, or a knitted fabric manufactured using each of calcium carboxymethyl cellulose fibers alone, chitosan compound fibers alone, or mixtures thereof, and optionally, in addition to these fibers, the substrate may further include various types of natural or artificial fibers or powder within the applicable scope for medical use.

Furthermore, the coating layer may be disposed on at least one of one surface, two surfaces, and an inside of the substrate, and the coating layer may include calcium carboxymethyl cellulose powder alone, chitosan compound powder alone, or mixtures thereof.

In case that the medical fibrous structure according to an embodiment of the present disclosure includes a substrate including fibers formed of at least one of calcium carboxymethyl cellulose and a chitosan compound; and a coating layer formed on the substrate, the coating layer including powder formed of at least one of calcium carboxymethyl cellulose and a chitosan compound, when the average particle diameter of the powder is larger than the size of the space formed between fibers in the substrate, the coating layer may be only formed on the surface of the nonwoven fabric. Furthermore, when powder having an average particle diameter that is smaller than the size of the space formed between fibers in the substrate and powder having a larger average particle diameter is mixed together, some of the powder may be formed as a coating layer in the substrate, and the remaining powder may be formed as a coating layer on the surface of the substrate.

According to an embodiment of the present disclosure, in case that the coating layer is formed on at least one surface of the substrate, the coating layer may be formed on one surface of the substrate in whole or in part, and when the coating layer is formed on one surface of the substrate in whole or in part, the coating layer may be formed as a patterned layer in various three-dimensional shapes with different thicknesses.

For example, if the coating layer is formed as a patterned layer of water-soluble chitosan compound powder on at least one surface of the substrate as described above, hemostatic effect and blood absorption rate of chitosan compound powder can be improved and hemostatic effect can be further improved by rapid releasing of calcium ions from calcium carboxymethyl cellulose in contact with body fluid or blood. Otherwise, since hemostatic effect may be reduced by preventing blood from being absorbed into the inside of the medical fibrous structure, which is caused by excessive dissolving of the water-soluble chitosan only on the surface of the medical fibrous structure with contact of water, body fluid, or blood.

The patterned layer may be one selected from the group consisting of dot, circle, polygon, doughnut, stripe, step, concavo-convex and grid patterns, or combinations thereof, and in addition to this, may be a variety of formless patterns with no regular uniform pattern.

According to an embodiment of the present disclosure, in case that a complex patterned layer formed of a larger load amount of chitosan compound powder and a smaller load amount of chitosan compound powder is used, the hemostatic effect and the blood absorption rate of chitosan compound powder can be improved, or when contacted with body fluid or blood, calcium ions are released quickly from calcium carboxymethyl cellulose, further exerting a hemostatic effect.

A more preferable example of the complex patterned layer may be a step or concavo-convex pattern.

Furthermore, the medical fibrous structure may be a microfibril structure including microfibrils formed of at least one of calcium carboxymethyl cellulose and a chitosan compound; and powder formed of at least one of calcium carboxymethyl cellulose and a chitosan compound.

Furthermore, as described in the foregoing, the microfibril structure may include microfibrils and powder such that the powder is present between the microfibrils mechanically entangled without a special shape, and the microfibril structure may be used in the manner of stacking on cotton tufty, particulate, and powdery structure reinforcement in various sizes at a wound site. Furthermore, to easily remove after hemostasis treatment is completed, components used in the microfibril structure such as microfibrils may be dissolved when contacted with a saline solution, body fluid or blood.

The calcium carboxymethyl cellulose as used herein refers to calcium carboxymethyl cellulose in which divalent calcium ions are bonded with carboxyl groups of carboxymethyl cellulose.

The carboxymethyl cellulose as used herein refers to cellulose whose a hydroxyl group of glucose is substituted by a carboxymethyl group. Carboxymethyl cellulose is used in various fields including glues, foods, cosmetics, drug additives and extraction of petroleum because it has a thickening effect due to gelation occurring when contacted with water, and in particular, is widely used as medical materials because of high biocompatibility When the medical fibrous structure according to an embodiment of the present disclosure is a nonwoven fabric, calcium carboxymethyl cellulose fibers used in the nonwoven fabric may have an average length (average fiber length) of, for example, from 0.1 to 130 mm, from 0.1 to 40 mm, from 0.1 to 10 mm, or from 10 to 60 mm, and may have fineness of from 0.1 to 15 denier, or from 0.1 to 10 denier.

When the fiber length and the fineness satisfy these ranges, dispersion of fibers can be improved in the manufacture of a wet-laid nonwoven fabric, opening in a dry-laid nonwoven fabric manufacturing process is made easy, and shape stability can be improved.

Furthermore, as a result of analysis using EDX (Energy Dispersive X-Ray), the calcium carboxymethyl cellulose may have the calcium content of, for example, from 1 to 20 wt %, 2 to 12 wt %, or 5 to 10 wt % per the total weight of the calcium carboxymethyl cellulose. When the calcium content satisfies this range, the hemostatic performance is further enhanced and the rate of fluid absorption can be improved when contacted with blood.

The degree of substitution of calcium carboxymethyl cellulose may be, for example, from 0.4 to 3.0, from 0.6 to 2.5, or from 0.7 to 1.5. When the degree of substitution satisfies this range, calcium ions can be effectively introduced, and water swellability and dissolution of calcium ions can be improved when contacted with water or body fluid. Here, the degree of substitution represents how many hydroxyl groups of glucose that forms cellulose are substituted by carboxymethyl groups, and when one of three hydroxyl groups in cellulose on average is substituted by a carboxymethyl group, the degree of substitution is defined as 1.

The weight average molecular weight of calcium carboxymethyl cellulose may be, for example, from 10,000 to 250,000 g/mol, from 20,000 to 200,000 g/mol, or from 40,000 to 150,000 g/mol, and when the weight average molecular weight satisfies this range, the releasing behavior of calcium ions can be improved when contacted with body fluid while maintaining the fiber shape.

The chitosan compound is a compound in deacetylated form of chitin that is a key ingredient of shrimps, crabs, lobsters and cuttlefish, and is being sold in many forms for industrial applications.

The chitosan compound provides a positively charged surface having strong permeability and a high specific surface area, and the positively charged surface can form a surface that is highly reactive to red blood cell and platelet interactions. The red blood cell membrane has a negative charge, and is attracted to the positively charged surface of the chitosan compound, and the attracted red blood cell membrane and the chitosan compound are brought into contact and combination with each other, so clots can be formed very quickly. For this reason, the chitosan compound has very good blood coagulation properties, and is linked to bacteria, endotoxin, and microorganisms and exerts an effect on the killing of bacteria, microorganisms, and/or virus formulations.

According to an embodiment of the present disclosure, the degree of deacetylation of the chitosan compound may be, for example, from 60 to 100%, or from 80 to 100%, and the weight average molecular weight of the chitosan compound may be, for example, from 5,000 to 1,500,000 g/mol, or from 20,000 to 1,200,000 g/mol. Specifically, in the case of chitosan compound powder, the weight average molecular weight may be from 5,000 to 1,000,000 g/mol, and in the case of chitosan compound fibers, the weight average molecular weight may be from 500,000 to 1,500,000 g/mol. When the degree of deacetylation and the weight average molecular weight satisfy these ranges, a hemostatic effect and a wound healing effect can be further enhanced. In case that the chitosan compound is soluble in water, when the molecular weight is from 5,000 to 500,000 g/mol, water solubility can be further improved.

The chitosan compound may be at least one of chitosan fibers and chitosan powder.

In this instance, when the chitosan compound is chitosan fibers, the chitosan fibers may have an average fiber length of, for example, from 0.1 to 130 mm, from 0.1 to 40 mm, from 0.1 to 10 mm, or from 10 to 60 mm, and may have fineness of, for example, from 0.1 to 10 denier, or from 0.5 to 5 denier. When the chitosan fibers have such average length and fineness, the ability to form a nonwoven fabric is superior and a hemostatic effect can be enhanced.

Furthermore, when the chitosan compound is chitosan powder, the chitosan powder may have an average particle diameter of, for example, from 1 to 1,000□, from 10 to 1,000□, or from 100 to 800□, and when the average particle diameter of the chitosan powder satisfies this range, a hemostatic effect can be improved, and a separation phenomenon occurring when mixing with the calcium carboxymethyl cellulose fibrous structure can reduce.

According to an embodiment of the present disclosure, the chitosan compound may be insoluble in water or soluble in water. Specifically, the chitosan compound fibers may be insoluble in water, and the chitosan compound powder may be soluble in water.

In this instance, the chitosan compound fibers being insoluble in water signifies that chitosan compound fibers do not dissolve in neutral water, and dissolve in water when the pH is reduced to, for example, pH 6.5 or less, with an addition of acids.

On the other hand, the chitosan compound powder being soluble in water signifies that chitosan compound powder dissolves in neutral water, namely, chitosan compound powder dissolves in water without addition of acids for dissolution.

The chitosan compound may be at least one of chitosan and chitosan derivatives, and the chitosan derivatives may include carboxymethyl chitosan or its salt, and trimethyl chloride chitosan.

Furthermore, the water-soluble chitosan compound includes, but is not limited to, derivatives of water-soluble chitosan lactate, water-soluble chitosan hydrochloride, water-soluble chitosan ascorbate, and low-molecular weight water-soluble chitosan. The derivatives of water-soluble chitosan include, for example, chitosan-PEG and chitosan-bile acid.

In the medical fibrous structure, a weight ratio of the calcium carboxymethyl cellulose and the chitosan compound may be from 99:1 to 1:99, from 90:10 to 10:90, from 80:20 to 20:80, or from 70:30 to 30:70. When the weight ratio satisfies this range, the shape stability is superior, the rate of fluid absorption is fast, and a thickening effect is improved, contributing to the outstanding hemostatic effect.

The medical fibrous structure according to an embodiment of the present disclosure may have the blood absorption rate of 60 seconds or less, preferably 10 seconds or less, and more preferably 3 seconds or less.

In this instance, the blood absorption rate is evaluated as the time required for 100□ of blood to be completely absorbed by a medical fibrous structure of dimensions 1 cm×1 cm (width×length) after the blood was dripped into the medical fibrous structure.

Furthermore, the medical fibrous structure according to an embodiment of the present disclosure may have absorbance of 0.30 or less, preferably 0.25 or less, more preferably 0.20 or less, and even more preferably 0.10 or less when evaluating the blood coagulation properties.

In this instance, the blood coagulation property evaluation was conducted by dripping 100□ of a mixed solution of blood and an anticoagulant (sodium citrate, 3.8 w/v %) at a volume ratio of 9:1 into a medical fibrous structure of dimensions 1 cm×1 cm (width×length), inducing coagulation in a 37° C. incubator for 10 minutes with the addition of 10□ of 0.2M $CaCl_2$ aqueous solution, and allowing some of the blood that did not participate in coagulation to be eluted in 12.5 mL of distilled water again. 200□ of the eluate was taken and measured to determine absorbance [AB] at 540 nm wavelength, 200□ of distilled water was measured to determine absorbance [AW] at 540 nm wavelength, and calculation was performed by the following equation to obviate the influence of distilled water included in the blood eluate on absorbance:

Absorbance for evaluation of blood coagulation properties=Absorbance of blood eluate [AB]−Absorbance of distilled water [AW].

Furthermore, according to an embodiment of the present disclosure, the medical fibrous structure may have absorbance of 0.3 or less when evaluating the blood coagulation properties on the condition of the coagulation time of 5 minutes in an incubator as below.

The specific evaluation condition of blood coagulation properties was that 100□ of a mixed solution of blood and an anticoagulant (sodium citrate, 3.8 w/v %) at a volume ratio of 9:1 was dripped into a medical fibrous structure of dimensions 1 cm×1 cm (width×length) and coagulated in a 37° C. incubator for 5 minutes with the addition of 100 of 0.2M $CaCl_2$ aqueous solution, blood not having participated in coagulation was eluted in 12.5 mL of distilled water again, 200□ of the eluate was taken and measured to determine absorbance [AB] at 540 nm wavelength, 200□ of distilled water was measured to determine absorbance [AW] at 540 nm wavelength, and calculation was performed by the following equation to obviate the influence of distilled water included in the blood eluate on absorbance:

Absorbance for evaluation of blood coagulation properties=Absorbance of blood eluate [AB]−Absorbance of distilled water [AW]

Furthermore, the medical fibrous structure according to an embodiment of the present disclosure may further include an additive, and the additive may be freely selected according to the required properties, and its examples include bioactive materials, plasticizers, hemostatic materials, antimicrobial materials, cells, enzymes, antigens, and pigments.

According to an embodiment of the present disclosure, a non-toxic plasticizer glycerol may be mixed in optimal amounts to increase the flexibility or adhesive strength of the medical fibrous structure, or antimicrobial materials such as silver, silver-based compounds, triclosan, biguanides, and methylene blue may be added to prevent the invasion of microorganisms such as bacteria into the skin.

Furthermore, the bioactive material as used herein refers to a material that greatly affects the functions of the body in trace amounts, and includes vitamins, hormones, enzymes, and neurotransmitters, for example, including, but not limited to, human serum albumen, bovine thrombin, human thrombin (h thrombin), rh thrombin, factor VIIa, factor XIII, recombinant factor XIII (rFXIII), thromboxane A2, prostaglandin-2a, epidermal growth factor, platelet-derived growth factor, von Willebrand factor, tumor necrosis factor (TNF), TNF-alpha, transforming growth factor (TGF), TGF-alpha, TGF-beta, insulin-like growth factor, fibroblast growth factor, keratinocyte growth factor, nerve growth factor, penicillin, ampicillin, methicillin, amoxicillin, clavamox, clavulanic acid, aztreonam, imipenem, streptomycin, kanamycin, tobramycin, gentamicin, vancomycin, clindamycin, erythromycin, polymyxin, bacitracin, amphotericin, nystatin, rifampicin, tetracycline, doxycycline, chloramphenicol and combinations thereof, depending on the nature of wounds or medical conditions of patients. As the hemostatic material, collagen, gelatin, alginate, oxidized cellulose, chitin and chitin derivatives, chitosan derivatives, and calcium chloride may be added.

Furthermore, the medical fibrous structure according to an embodiment of the present disclosure can be used as hemostatic agents for filling holes and openings in the body due to having superior physical properties, and the calcium carboxymethyl cellulose and the water-soluble chitosan compound disintegrate over time when contacted with body fluids which eliminates the need for removal after treatment, so it is expected that applicability as implantable hemostatic agents will be high.

A structure reinforcement may be further included on at least one of at least one surface of the medical fibrous structure and an inside of the medical fibrous structure.

The content of the structure reinforcement further added may be 5 to 100 parts by weight, 5 to 50 parts by weight, or 10 to 40 parts by weight per 100 parts by weight of the mixture of the calcium carboxymethyl cellulose and the chitosan compound. When the content of the structure reinforcement satisfies this range, shape stability can be improved while reducing the decrease of hemostatic effect.

The structure reinforcement may be variously used in at least one form of a structure reinforcing particle, a structure reinforcing fiber, and a structure reinforcing substrate.

According to an embodiment of the present disclosure, the medical fibrous structure may be formed as a nonwoven fabric, a knitted fabric, a woven fabric and a microfibril structure, having the added structure reinforcement in the form of particles or fibers, with the calcium carboxymethyl cellulose and the chitosan compound.

Furthermore, the medical fibrous structure according to an embodiment of the present disclosure may further include a structure reinforcing substrate on at least one surface of the medical fibrous structure in various forms as described above.

The structure reinforcing substrate may be a woven fabric, a knitted fabric, a nonwoven fabric, a film, a foam, or a sponge of different material, and may serve to enhance shape stability and bonding strength of the medical fibrous structure.

The structure reinforcement has a structure reinforcing function that may be introduced by hot air bonding, chemical bonding, mechanical bonding and ultrasonic bonding, and materials of the structure reinforcement include, but are not limited to, synthetic fibers having a predetermined melting point such as polyester, nylon, polypropylene, polyethylene, polylactic acid, polyglycolic acid, polydioxanone, polycaprolactone, and polyvinylalcohol, or natural or regenerated fibers such as cotton and viscose rayon.

According to another aspect of the present disclosure, there is provided a process for preparing a medical fibrous structure, wherein the medical fibrous structure includes calcium carboxymethyl cellulose and a chitosan compound, and at least one of the calcium carboxymethyl cellulose and the chitosan compound is in fibrous form.

The preparing process may include preparing a nonwoven fabric, a woven fabric, or a knitted fabric including calcium carboxymethyl cellulose fibers and chitosan compound fibers.

According to an embodiment of the present disclosure, the preparing of a nonwoven fabric may include mixing the calcium carboxymethyl cellulose fibers and the chitosan compound fibers to prepare a mixture; adding a dispersion medium to the mixture and blending them; and removing the dispersion medium.

Furthermore, the preparing process may include preparing a substrate including fibers formed of at least one of calcium carboxymethyl cellulose and a chitosan compound; and forming a fiber layer including fibers formed of at least one of calcium carboxymethyl cellulose and a chitosan compound on at least one of at least one surface of the substrate and an inside of the substrate, and the substrate may be a nonwoven fabric, a woven fabric, or a knitted fabric.

For example, in case that the substrate is a nonwoven fabric, the preparing process may include adding a dispersion medium to fibers formed of at least one of the calcium carboxymethyl cellulose and the chitosan compound and blending them; removing the dispersion medium to prepare a nonwoven fabric; and forming a fiber layer including fibers formed of at least one of the calcium carboxymethyl cellulose and the chitosan compound on at least one of at least one surface of the nonwoven fabric and an inside of the nonwoven fabric.

According to an embodiment of the present disclosure, the preparing process may include a microfibril structure including calcium carboxymethyl cellulose microfibrils and chitosan compound microfibrils.

For example, the process for preparing a microfibril structure may include putting the calcium carboxymethyl cellulose fibers and the chitosan fibers in a blend mixer or a grinder and milling them by strong rotation to prepare a microfibril structure in which the two ingredients are mixed.

According to an embodiment of the present disclosure, the preparing process may include preparing a substrate including fibers formed of at least one of calcium carboxymethyl cellulose and a chitosan compound; and forming a coating layer including powder formed of at least one of calcium carboxymethyl cellulose and a chitosan compound on at least one of at least one surface of the substrate and an inside of the substrate, and the substrate may be a nonwoven fabric, a woven fabric, or a knitted fabric.

In this instance, in case that the substrate is a nonwoven fabric, the preparing process may include adding a dispersion medium to fibers formed of at least one of the calcium carboxymethyl cellulose and the chitosan compound and blending them; removing the dispersion medium to prepare a nonwoven fabric; and forming a coating layer including powder formed of at least one of the calcium carboxymethyl cellulose and the chitosan compound on at least one of at least one surface of the nonwoven fabric and an inside of the nonwoven fabric.

Furthermore, according to an embodiment of the present disclosure, the process for preparing a nonwoven fabric includes a process for preparing a dry-laid nonwoven fabric by a powder scattering method.

In case that the nonwoven fabric is formed of chitosan compound fibers, the process for preparing a medical fibrous structure according to an embodiment of the present disclosure may include opening the chitosan compound fibers by a carding method; dispersing the calcium carboxymethyl cellulose powder or microfibrils in a space formed between the opened chitosan compound fibers by a scattering method; and needle punching the chitosan compound fibers mixed with the calcium carboxymethyl cellulose powder or microfibrils. As a result, a medical fibrous structure may be prepared in which the calcium carboxymethyl cellulose powder or microfibrils are present on at least one surface and an inside of a nonwoven fabric formed of the chitosan compound fibers prepared by a needle punching method. Furthermore, the opening of the chitosan compound fibers, during carding process, may further include mixing with more hydrophilic fibers.

In the preparing process according to an embodiment of the present disclosure, a weight ratio of the calcium carboxymethyl cellulose and the chitosan compound is 99:1 to 1:99, and may be 90:10 to 10:90, 80:20 to 20:80, or 70:30 to 30:70.

According to an embodiment of the present disclosure, the calcium carboxymethyl cellulose may be prepared by mixing at least one selected from sodium carboxymethyl cellulose and carboxymethyl cellulose with a solution including water, a non-solvent for sodium carboxymethyl cellulose, and a calcium compound.

The non-solvent for sodium carboxymethyl cellulose includes methanol, ethanol, isopropyl alcohol, acetone, methylene chloride, ethyl acetate, and chloroform. For example, the non-solvent may be alcohol. The reason that a solvent used in treating with calcium ions is a mixed solvent of water and a non-solvent for sodium carboxymethyl cellulose is to increase the efficiency of introduction of calcium ions in aqueous solution phase, and prevent sodium carboxymethyl cellulose or carboxymethyl cellulose from losing its fiber or powder shape after being dissolved or gelled by excess water used in the treatment process.

In this instance, the sodium carboxymethyl cellulose or carboxymethyl cellulose may be prepared by from cellulose by treatment with alkali and reaction with monochloroacetate or its salt. The cellulose to be carboxymethylated includes any one selected from the group consisting of viscose rayon, cotton, wood pulp, and lyocell.

The mixed solution including water and a non-solvent for sodium carboxymethyl cellulose may be prepared as a mixed solution in which a non-solvent and water are mixed, for example, at a volume ratio of 70:30 to 95:5 or 75:25 to 90:10.

In this instance, the calcium compound includes, but is not limited to, at least one selected from the group consisting of calcium chloride, calcium carbonate, calcium citrate, calcium gluconate, glubionate calcium, calcium hydroxide, and calcium oxalate.

Subsequently, sodium carboxymethyl cellulose or carboxymethyl cellulose is added to the solution including water, the non-solvent for sodium carboxymethyl cellulose, and the calcium compound, and is shaked using a shaker to obtain calcium carboxymethyl cellulose. In this instance, to increase the reaction efficiency, heating may be performed.

The content of the calcium compound in the calcium compound solution may be a molar ratio of 0.25 or more, 0.5 or more, or 1 or more, relative to sodium carboxymethyl cellulose or carboxymethyl cellulose. When the amount of calcium compound satisfies this range, calcium carboxymethyl cellulose having an optimal content of calcium ions can be prepared.

Subsequently, the obtained calcium carboxymethyl cellulose may be washed using a mixed solution including water and a non-solvent for calcium carboxymethyl cellulose, and additionally washed with a non-solvent for calcium carboxymethyl cellulose again, and subsequently, may be dried.

The non-solvent for calcium carboxymethyl cellulose may be alcohol. The alcohol includes, but is not limited to, methanol, ethanol, propanol and mixtures thereof.

The calcium carboxymethyl cellulose mentioned in the preparing process may be in the form of fibers (including microfibrils), powder, a nonwoven fabric, a woven fabric, or a knitted fabric.

In the process for preparing a medical fibrous structure as described in the foregoing, the dispersion medium may be a mixed solvent including a non-solvent for calcium carboxymethyl cellulose and water, and a volume ratio of the non-solvent for calcium carboxymethyl cellulose and the water may be, for example, 70:30 to 95:5 or 75:25 to 90:10.

Hereinafter, the process for preparing a medical fibrous structure according to an embodiment of the present disclosure will be described in more detail.

The process for preparing a medical fibrous structure according to an embodiment of the present disclosure may be prepared by various methods depending on the type of the chitosan compound used, chitosan fibers or chitosan powder.

For example, in case that the medical fibrous structure itself or the substrate includes a nonwoven fabric, it may be prepared by a wet-laid nonwoven fabric preparation method, a dry-laid nonwoven fabric preparation method, or combination thereof.

The process for preparing a medical fibrous structure with the wet-laid nonwoven fabric may include mixing the calcium carboxymethyl cellulose fibers and the chitosan compound to prepare a mixture; adding a dispersion medium or a medium for dispersion to the mixture and blending them; and removing the dispersion medium.

Furthermore, in case that the chitosan compound is chitosan compound fibers, the process for preparing a nonwoven fabric medical fibrous structure may include preparing a chitosan compound nonwoven fabric by a dry-laid nonwoven fabric preparation method such as needle punching after carding the chitosan compound fibers and air laid methods or a wet-laid nonwoven fabric preparation method; dispersing the calcium carboxymethyl cellulose fibers in a dispersion medium including water and a non-solvent for calcium carboxymethyl cellulose fibers; removing the dispersion medium, using the chitosan compound fibers as a screen mesh of a wet-laid nonwoven process, to prepare a medical fibrous structure of calcium carboxymethyl cellulose fibers.

Furthermore, when preparing a nonwoven fabric by a dry-laid method such as needle punching after carding using the chitosan compound fibers, the carding process may include dispersing the calcium carboxymethyl cellulose fibers to prepare a nonwoven fabric medical fibrous structure.

Furthermore, the process may include preparing a nonwoven fabric from calcium carboxymethyl cellulose fibers by a wet-laid nonwoven fabric preparation process or a dry-laid nonwoven fabric preparation process, or preparing a calcium carboxymethyl cellulose nonwoven fabric by chemically treating a cellulose nonwoven fabric, and dispersing chitosan compound fibers in a dispersion medium including water and a non-solvent for calcium carboxymethyl cellulose fibers; and removing the dispersion medium from the chitosan compound fibers by a wet-laid nonwoven fabric preparation method using the calcium carboxymethyl cellulose fibers as a screen mesh to prepare a medical fibrous structure.

Furthermore, in case that the chitosan compound is chitosan compound powder, a medical fibrous structure may be prepared by preparing a nonwoven fabric, a woven fabric, a knitted fabric, and a microfibril structure using calcium carboxymethyl cellulose first, and introducing chitosan compound powder for a coating layer, or by mixing chitosan compound powder with calcium carboxymethyl cellulose fibers. In this instance, for the calcium carboxymethyl cellulose fibers, fibers with various average fiber lengths including microfibrils may be applied.

That is, in the former case in which chitosan compound powder is introduced for a coating layer, the process for preparing a nonwoven fabric medical fibrous structure may include preparing a nonwoven fabric formed of calcium carboxymethyl cellulose fibers by a wet-laid nonwoven fabric preparation process or a dry-laid nonwoven fabric preparation process; and forming a coating layer including the chitosan compound powder on at least one of at least one surface of the calcium carboxymethyl cellulose nonwoven fabric and an inside of the nonwoven fabric.

In this instance, the step for forming a coating layer including chitosan compound powder may include stacking the chitosan compound powder on at least one surface of the calcium carboxymethyl cellulose nonwoven fabric and an inside of the nonwoven fabric, and applying water vapor to the nonwoven fabric having the stacked chitosan compound powder to bind the chitosan compound powder to the nonwoven fabric. The method for applying water vapor includes, for example, a method for applying water vapor or water particles using a method for applying steam to the nonwoven fabric or a method for spraying a small amount of water. In this instance, water vapor or water molecules are used to increase the bonding strength between the chitosan compound and the calcium carboxymethyl cellulose by dissolving a portion of the chitosan compound or the calcium carboxymethyl cellulose, and instead of water vapor or water particles, binder materials may be added.

Furthermore, in the latter case in which chitosan compound powder is mixed with calcium carboxymethyl cellulose fibers or microfibrils, the process for preparing a wet-laid nonwoven fabric medical fibrous structure may include blending calcium carboxymethyl cellulose fibers, chitosan powder, and a dispersion medium; and removing the dispersion medium.

The dispersion medium used to prepare a wet-laid nonwoven fabric medical structure may be a mixed solvent of water and a non-solvent for calcium carboxymethyl cellulose fibers. The non-solvent for calcium carboxymethyl cellulose fibers includes methanol, ethanol, isopropyl alcohol, acetone, methylene chloride, ethyl acetate, and chloroform. For example, the solvent may be a mixed solvent of water and alcohol, and in this instance, a volume ratio of alcohol and water may be, for example, 70:30 to 95:5 or 75:25 to 90:10. When the volume ratio of alcohol and water satisfies this range, it is possible to prevent calcium carboxymethyl cellulose fibers from losing the fiber shape after being dissolved or gelled by excess water.

Furthermore, the alcohol includes, but is not limited to, methanol, ethanol, propanol and mixtures thereof.

According to an embodiment of the present disclosure, the process may include preparing a microfibril structure, for example, in cotton tufty and particulate form, composed of calcium carboxymethyl cellulose fibers and a chitosan compound, from the calcium carboxymethyl cellulose fibers and the chitosan compound (fibers or powder) using a blend mixer. In this instance, to increase water solubility and consequentially a hemostatic effect, the chitosan compound may be water-soluble chitosan powder.

Furthermore, according to an embodiment of the present disclosure, as described above, the process may further include adding a structure reinforcement during or after preparation of a medical fibrous structure. Through the step for adding a structure reinforcement, shape stability of the medical fibrous structure, and bonding strength between fibers or fiber and powder can be enhanced. A detailed description of the structure reinforcement is the same as above.

According to an embodiment of the present disclosure, the process may further include a thermal bonding, heat compress or calendering step after preparing the nonwoven fabric medical fibrous structure by the above method. This additional step can increase the strength of the obtained medical fibrous structure in dry or wet state, and adjust the rate of fluid absorption.

The thermal bonding or calendering step may be performed under the temperature condition of 0 to 200° C. or 60 to 150° C., the nip pressure of 20 to 250 kg/cm or 1 to 50 N/cm$^2$, or the pressure condition of 0.01 to 2 tons.

According to an embodiment of the present disclosure, a gamma radiation step may be additionally performed after preparing the medical fibrous structure.

The gamma radiation step provides a sterilization for the medical fibrous structure, which is directly applied to the skin, without using heat or chemicals. Particularly, gamma radiation can be performed even on the medical fibrous structure that is sealed into a final product. The gamma radiation may be performed, for example, at the dose of from 5 to 30 kGy.

Hereinafter, the present disclosure will be described in detail through examples to help understanding. However, the embodiments of the present disclosure may be modified in many different forms, and the scope of the present disclosure should not be construed as being limited to the following examples. The embodiments of the present disclosure are provided to more fully explain the present disclosure to those having ordinary knowledge in the art to which the present disclosure pertains.

Example 1

<Step 1> Preparation of Sodium Carboxymethyl Cellulose Fiber and Preparation of Calcium Carboxymethyl Cellulose Fiber According to Korean Patent No. 10-1361629, viscose rayon fibers were alkalized and reacted with monochloroacetate, using isopropyl alcohol as a reaction medium, to prepare sodium carboxymethyl cellulose fibers (Degree of substitution 0.9).

Subsequently, CaCl$_2$ was dissolved in 1,000 mL of a mixed solution of ethanol (94.5%) and distilled water mixed at a volume ratio of 80:20 to prepare 0.06 mol/L solution, 10 g of the prepared sodium carboxymethyl cellulose (CMC) fibers were added thereto and treated at room temperature for about 60 minutes using a shaker to prepare calcium carboxymethyl cellulose fibers. The prepared calcium carboxymethyl cellulose fibers were washed using a mixed solution (80/20 v/v) of ethanol and distilled water for 30 minutes twice, and subsequently, were washed with 99.5% methanol twice for 10 minutes each time to remove water. The washed calcium carboxymethyl cellulose fibers were sufficiently dried at 60° C. in a vacuum oven. In this instance, the obtained calcium carboxymethyl cellulose fibers had an average fiber length of about 2 mm and the calcium content was 8.23% on the basis of 100 parts by weight of calcium carboxymethyl cellulose when measured by EDX.

<Step 2> Preparation of Wet-Laid Nonwoven Fabric

Chitosan fibers (NTPIA corporation, 3 denier, Degree of deacetylation 87% Molecular weight 1,000,000 g/mol) were dispersed in water and fed into a rotary grinding mill (Mass collider) to prepare chitosan fibers having an average fiber length of 1 mm. The calcium carboxymethyl cellulose fibers and the chitosan fibers were added at a ratio of 30:70 by weight to a blend mixer and strongly shaken to prepare a mixture consisting of 30 parts by weight of calcium carboxymethyl cellulose fibers and 70 parts by weight of chitosan fibers.

Figure 1B:
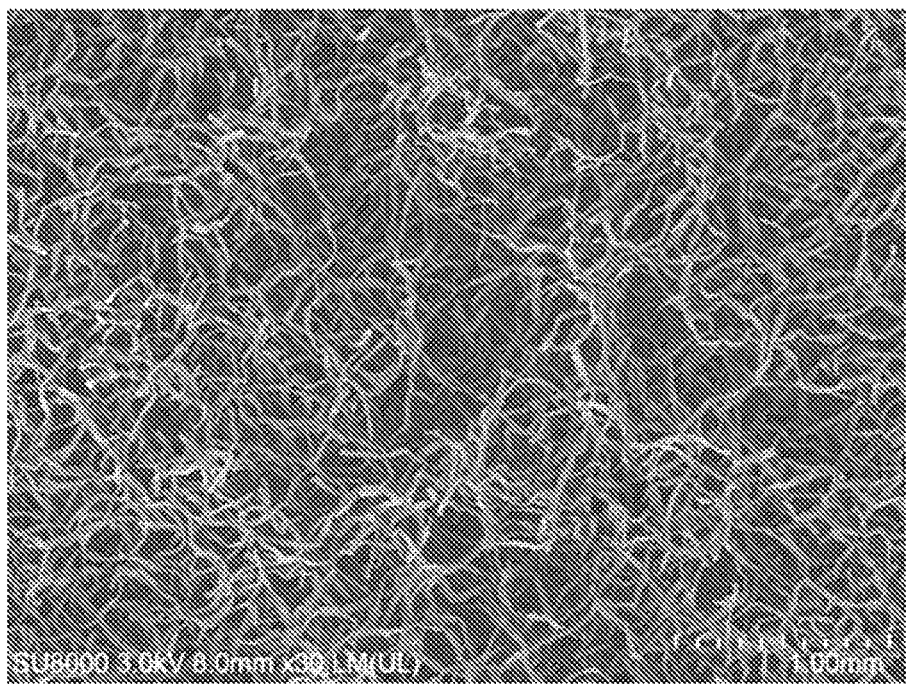
FIG. 1b is a SEM photographic image of a surface and a cross section of a medical fibrous structure prepared in example 1.
Figure 1B:
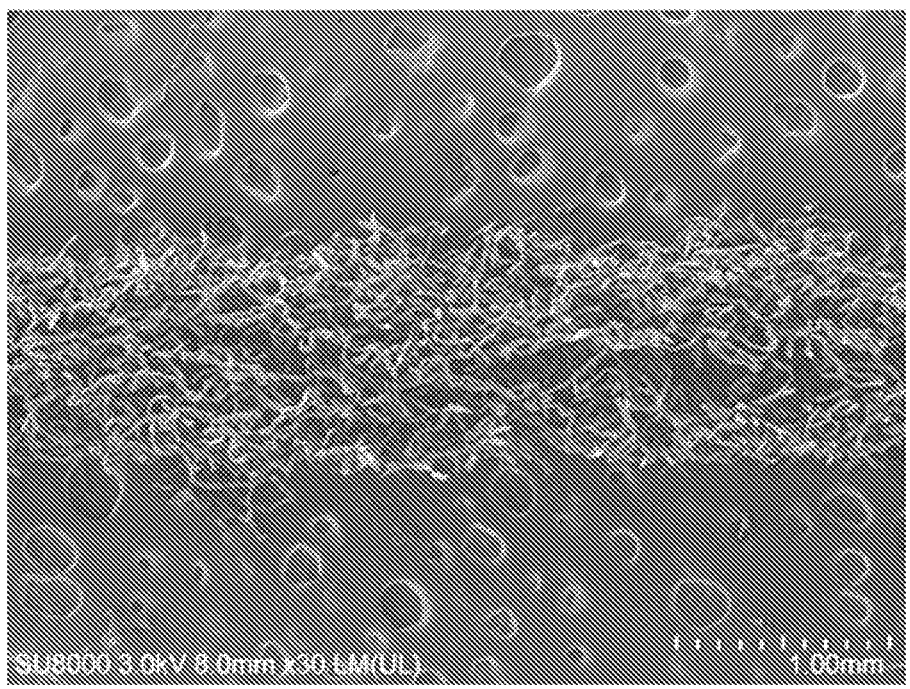

80 parts by volume of 99.5% methanol and 20 parts by volume of distilled water were mixed and strongly shaked by a shaker to prepare a mixed dispersion medium. The mixture prepared in the above step was added to the dispersion medium to prepare a solution for wet-laid nonwoven, followed by sufficient blending. The dispersion medium, i.e., the methanol/water solvent was removed using a hand sheet former to prepare 200 g/m$^2$ of a wet-laid nonwoven fabric formed of the calcium carboxymethyl cellulose fibers and the chitosan fibers mixed at a weight ratio of 30:70. Subsequently, the prepared nonwoven fabric was dried in a convection oven at 60° C. for 20 minutes to prepare a medical fibrous structure, and FIG. 1a shows an optical image of the medical fibrous structure, and FIG. 1b shows SEM images of the surface and cross section of the medical fibrous structure.

Example 2

Except using a mixture prepared by adding calcium carboxymethyl cellulose fibers and chitosan fibers at a weight ratio of 50:50 to a blend mixer, a medical fibrous structure composed of 50 parts by weight of calcium carboxymethyl cellulose fibers and 50 parts by weight of chitosan fibers was prepared by the same method as example 1.

Example 3

Except using a mixture prepared by adding calcium carboxymethyl cellulose fibers and chitosan fibers at a weight ratio of 70:30 to a blend mixer, a medical fibrous structure composed of 70 parts by weight of calcium carboxymethyl cellulose fibers and 30 parts by weight of chitosan fibers was prepared by the same method as example 1.

Example 4

Figure 2A:
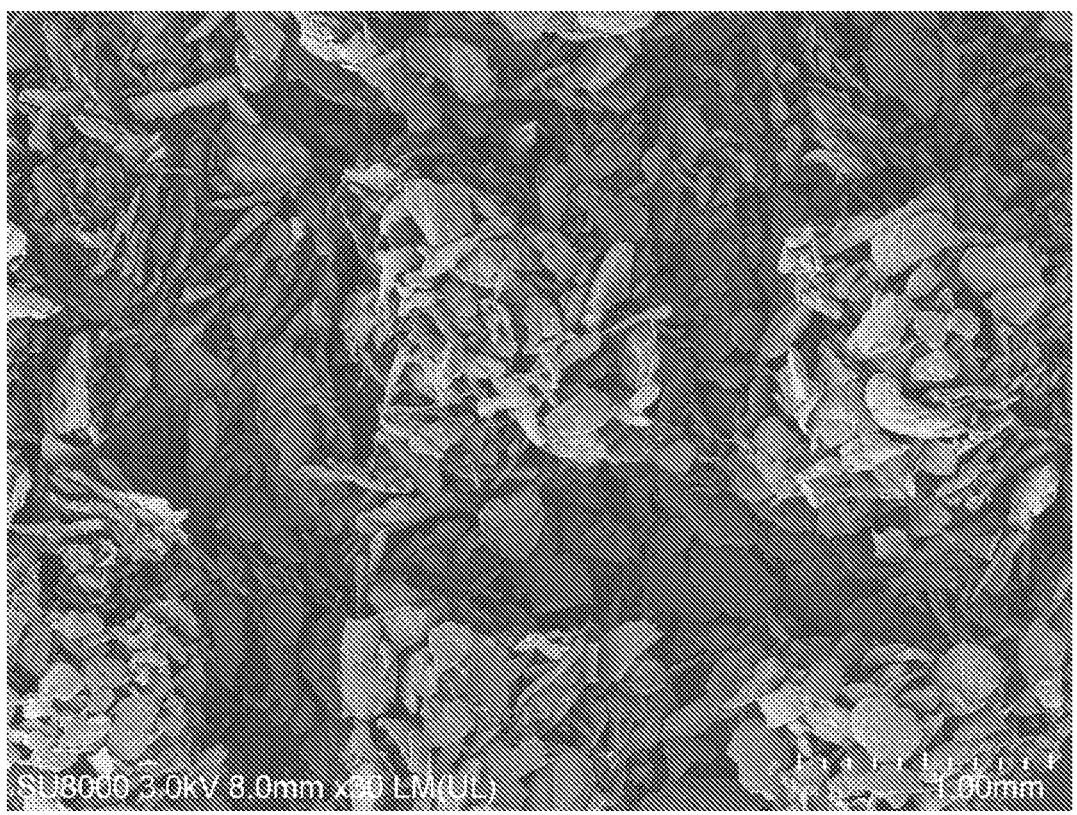
FIGS. 2a and 2b are SEM photographic images of a surface and a cross section of a medical fibrous structure prepared in example 4.
Figure 2B:
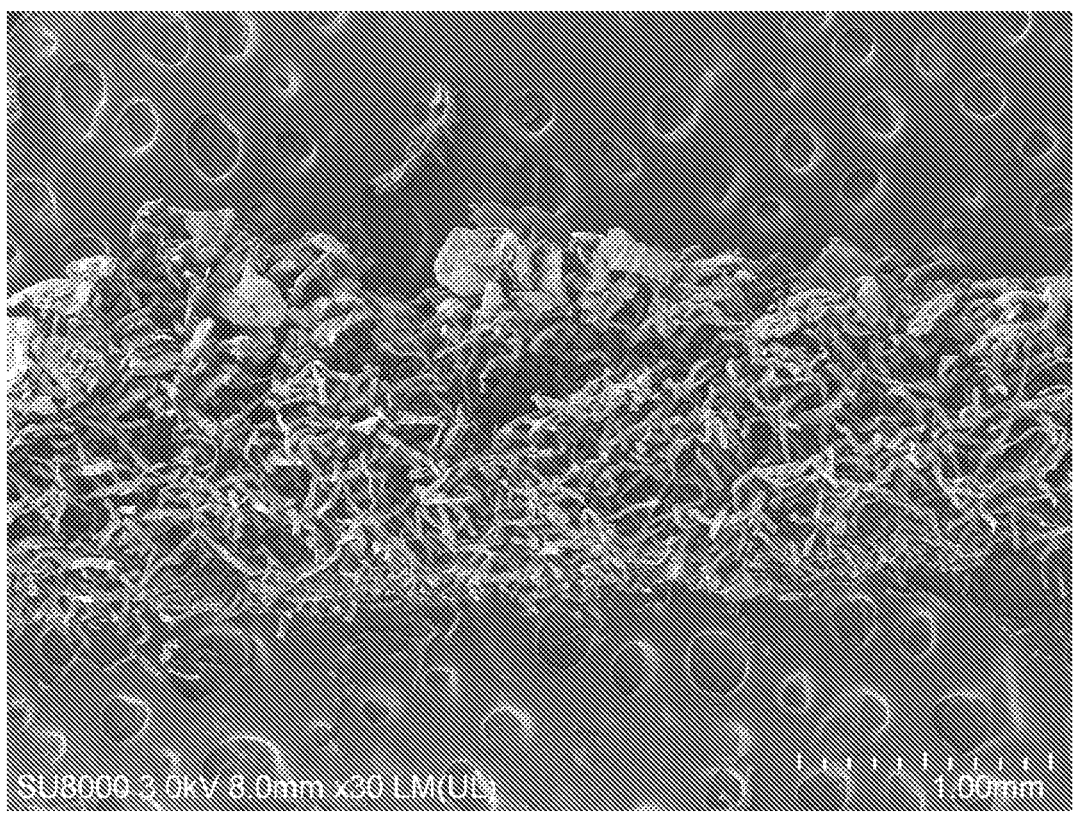

Calcium carboxymethyl cellulose fibers prepared by the same method as step 1 of example 1 were added to a mixed dispersion medium prepared by mixing 80 parts by volume of 99.5% methanol with 20 parts by volume of distilled water and strongly shaking, followed by sufficient blending, and the dispersion medium was removed using a hand sheet former to prepare 100 g/m$^2$ of calcium carboxymethyl cellulose nonwoven fabric. Subsequently, the prepared nonwoven fabric was dried at 60° C. #40 mesh was placed above the prepared calcium carboxymethyl cellulose nonwoven fabric, water-soluble chitosan powder (Average particle diameter 400☐, Degree of deacetylation 80%, Weight average molecular weight 350,000 g/mol) of the same weight as the prepared calcium carboxymethyl cellulose nonwoven fabric was uniformly stacked, the mesh was removed so that the powder was stacked at a relatively small thickness on the contact region with the mesh, and subsequently, steam was applied from the bottom of the nonwoven fabric to bind powder to the nonwoven fabric. The calcium carboxymethyl cellulose/chitosan composite nonwoven fabric of two-layered structure was dried at 60° C. in a convection oven to prepare 200 g/m² of a medical fibrous structure having a patterned stack structure, composed of 50 parts by weight of calcium carboxymethyl cellulose fibers and 50 parts by weight of chitosan powder, and FIGS. 2a and 2b each showed SEM images of the surface and cross section of the medical fibrous structure.

Example 5

Calcium carboxymethyl cellulose fibers prepared by the same method as step 1 of example 1 and water-soluble chitosan powder (Average diameter 400□, Degree of deacetylation 80%, Weight average molecular weight 350,000 g/mol) were added to a dispersion medium prepared by mixing 80 parts by volume of 99.5% methanol with 20 parts by volume of distilled water and strongly shaking by a shaker, at a 50:50 weight ratio of the calcium carboxymethyl cellulose fibers and the water-soluble chitosan powder, followed by sufficient blending, and the dispersion medium was removed using a hand sheet former to prepare 200 g/m² of a wet-laid nonwoven fabric in which the calcium carboxymethyl cellulose fibers and the chitosan powder were mixed. The calcium carboxymethyl cellulose/chitosan composite nonwoven fabric was dried at 60° C. in a convection oven to prepare a medical fibrous structure.

Example 6

Polyvinyl alcohol (PVA) fibers (KURARAY, 1 denier, Average fiber length: 3 mm) as structure reinforcing fibers were added to calcium carboxymethyl cellulose fibers prepared by the same method as example 1 and chitosan fibers in a blend mixer and strongly shaked to prepare a mixture consisting of 40 parts by weight of calcium carboxymethyl cellulose fibers, 40 parts by weight of chitosan fibers, and 20 parts by weight of polyvinyl alcohol fibers.

80 parts by volume of 99.5% methanol and 20 parts by volume of distilled water were mixed and strongly shaked by a shaker to prepare a mixed dispersion medium. The mixture prepared at the above step was added to the dispersion medium to prepare a solution for paper-making, followed by sufficient blending, and the dispersion medium was removed using a hand sheet former to prepare 250 g/m² of a wet-laid nonwoven fabric in which the calcium carboxymethyl cellulose fibers, the chitosan fibers and the polyvinyl alcohol fibers were mixed at a weight ratio 40:40:20. Subsequently, the prepared nonwoven fabric was dried in a convection oven at 90° C. for 20 minutes to prepare a medical fibrous structure.

Comparative Example 1

Chitosan fibers prepared by the same method as step 2 of example 1 were sufficiently blended with a dispersion medium, i.e., distilled water, and the dispersion medium was removed using a hand sheet former to prepare 200 g/m² of chitosan wet-laid nonwoven fabric. The prepared wet-laid chitosan nonwoven fabric was dried at 60° C. in a convection oven.

Comparative Example 2

Sodium carboxymethyl cellulose fibers (Degree of substitution 0.9) prepared as in step 1 of example 1 according to Korean Patent No. 10-1361629 was added to a mixed dispersion medium prepared by mixing 80 parts by volume of 99.5% methanol with 20 parts by volume of distilled water and strongly shaking, followed by sufficient blending, and the dispersion medium was removed using a hand sheet former to prepare 200 g/m² of a sodium carboxymethyl cellulose wet-laid nonwoven fabric. The prepared wet-laid sodium carboxymethyl cellulose nonwoven fabric was dried at 60° C. in a convection oven.

Comparative Example 3

Except using sodium carboxymethyl cellulose fibers prepared as in step 1 of example 1 according to Korean Patent No. 10-1361629 instead of calcium carboxymethyl cellulose fibers, a wet-laid nonwoven fabric was prepared by the same method as example 2.

Experimental Example: Observation to Determine Whether Calcium Ions were Introduced To find whether calcium ions were introduced by calcium treatment in <step 1> of example 1, carboxymethyl cellulose fibers before and after calcium treatment were coated with gold for 150 seconds using an ion coater (Ion Coater, E-1045), and images obtained by SEM observation of the surface using field emission scanning electron microscope (FE-SEM, SU 8010) and 6 repeated EDX measurements and elemental analysis are shown in each of FIGS. 3a and 3b.

Figure 3A:
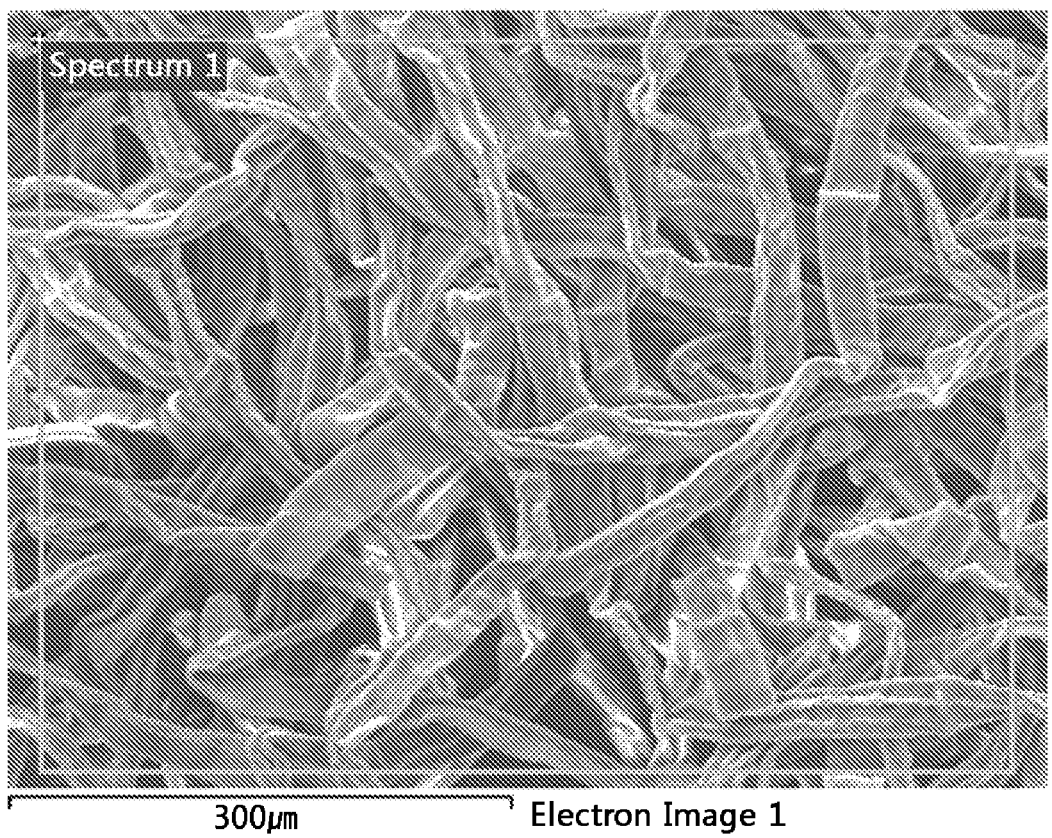
FIG. 3a is a photographic image of a surface of sodium carboxymethyl cellulose fibers before calcium treatment in example 1 observed using field emission scanning electron microscope (FE-SEM, SU 8010) and an image showing elemental analysis based on EDX measurements made six times repeatedly.
Figure 3A:
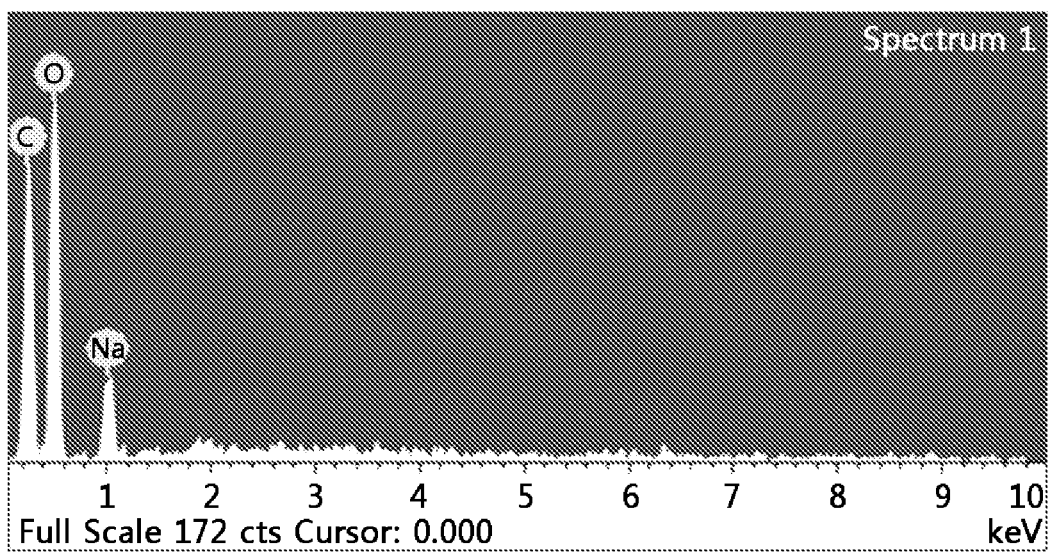
Figure 3B:
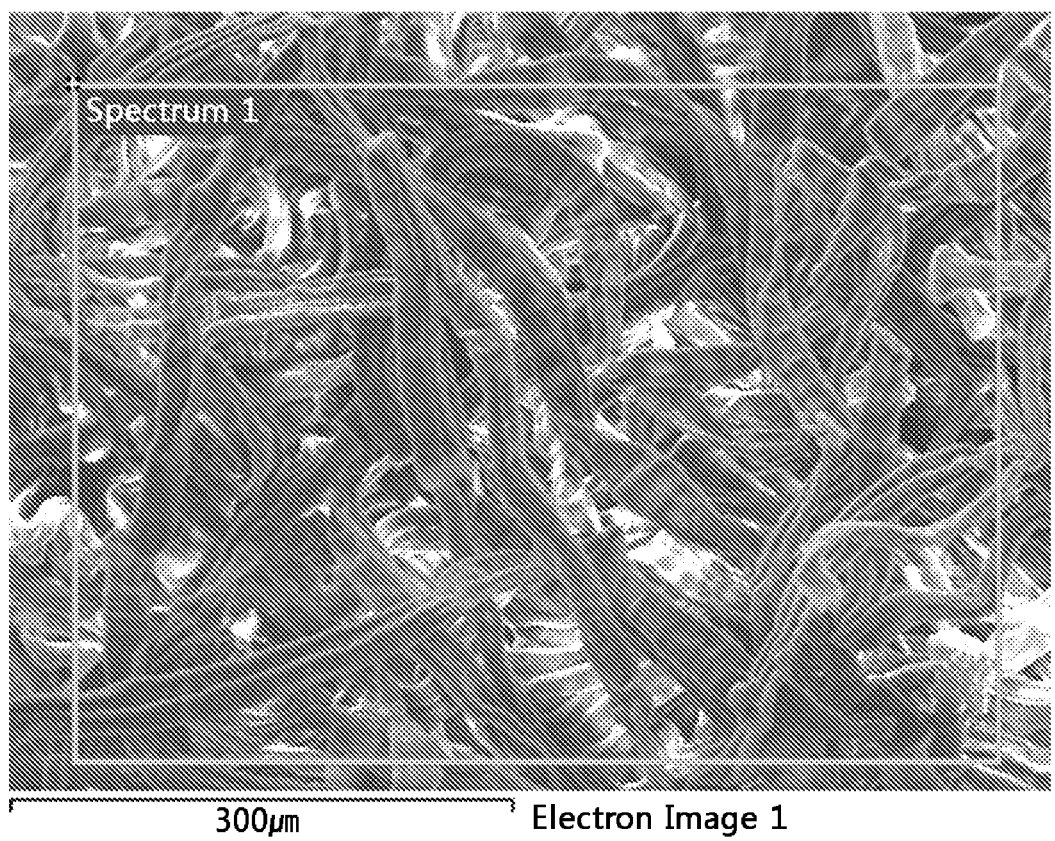
FIG. 3b is a photographic image of a surface of calcium carboxymethyl cellulose fibers after calcium treatment in example 1 observed using field emission scanning electron microscope (FE-SEM, SU 8010) and an image showing elemental analysis based on EDX measurements made six times repeatedly.
Figure 3B:
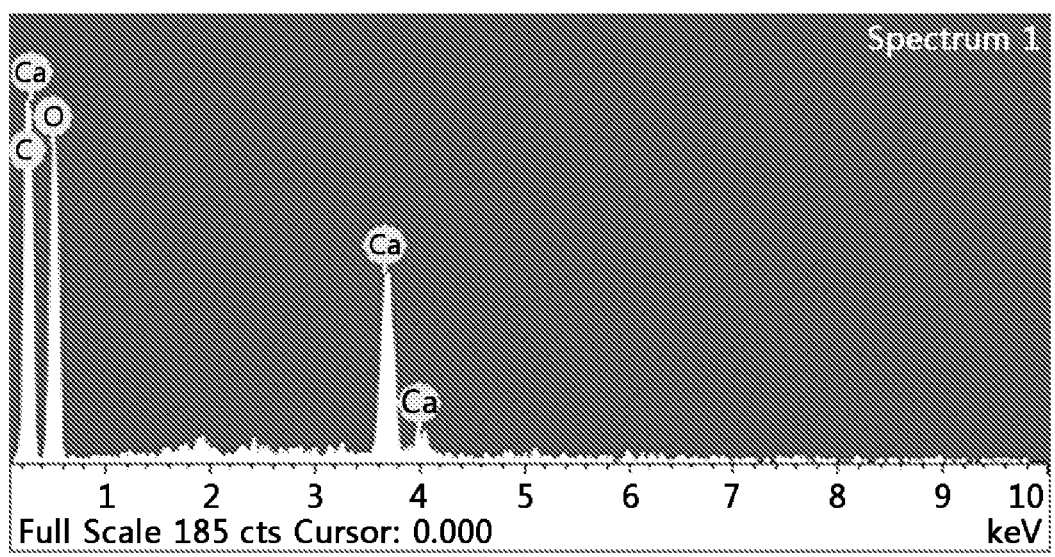

Referring to FIGS. 3a and 3b, there was no big difference in shape of carboxymethyl cellulose fiber between before and after calcium treatment. As a result of elemental analysis, in the case of before calcium treatment (FIG. 3a), Na atoms were detected from sodium carboxymethyl cellulose, and a weight ratio of 5.42% was detected and Ca atoms were not detected. As shown in FIG. 3b, in the case of after calcium treatment, Na atoms were not detected, and Ca atoms were detected and a weight ratio was 8.23%. From this, it could be seen that Ca ions were effectively introduced.

In the case of sodium carboxymethyl cellulose untreated with calcium ions, a gel blocking phenomenon occurs a bit, resulting in slow absorption, while in case that calcium ion is treated, calcium divalent ions form bonds with carboxyl groups of carboxymethyl cellulose, inducing crosslinking between carboxymethyl cellulose fibers, resulting in reductions in gel blocking phenomenon and very fast fluid absorption. Furthermore, calcium is released when contacted with blood, and it is expected to further promote blood coagulation.

Experimental Example: Evaluation of Blood Coagulation Properties—Coagulation Time 10 Minutes The blood coagulation properties were evaluated for the medical fibrous structures prepared in examples 1 to 6 and comparative examples 1 to 3, commercial hemostatic dressings in Table 1 (comparative examples 4 to 6), a cotton gauze (comparative example 7), and blood alone (comparative example 8).

TABLE 1

|  | Brand name | Manufacturer | Key ingredient |
|---|---|---|---|
| Comparative example 4 | SURGICEL | ETHICON | Oxidized regenerated cellulose |
| Comparative example 5 | HemCon Bandage | Hemcon Inc. | Chitosan foam |
| Comparative example 6 | QuikClot | Combat Medical Systems | Clay mineral (Kaolin) attached on gauze |

For the blood coagulation properties, 100□ of a mixed solution of blood and an anticoagulant (sodium citrate, 3.8 w/v %) at a 9:1 volume ratio was dripped into sample of dimensions 1 cm×1 cm (width×length) in cross section and coagulated in a 37° C. incubator for 10 minutes with the addition of 10□ of 0.2M $CaCl_2$ aqueous solution, and blood not having participated in coagulation was eluted in 12.5 mL of distilled water again. 200□ of the eluate was taken and measured to determine absorbance [AB] at 540 nm wavelength, and 200□ of distilled water was measured to determine absorbance [AW] at 540 nm wavelength, and to obviate the influence of distilled water included in the blood eluate on absorbance, absorbance was calculated by the following equation. In the case of comparative example 8, absorbance was measured using blood alone without any hemostatic dressing by the same method as above. The absorbance and photographic images of the evaluated results are shown in the following FIGS. 4 and 5 respectively.

Absorbance for evaluation of blood coagulation properties=Absorbance of blood eluate [AB]−Absorbance of distilled water [AW]

Figure 4:
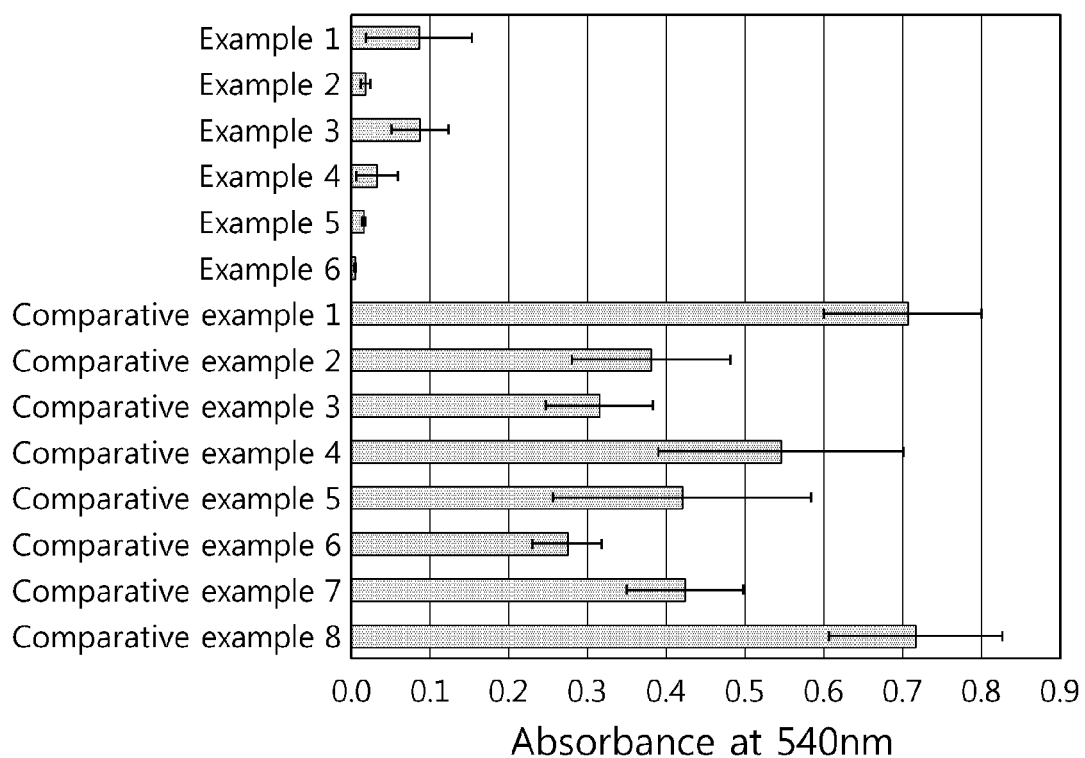
FIG. 4 is a graph showing blood coagulation property evaluation results of examples 1 to 6 and comparative examples 1 to 8.
Figure 5:
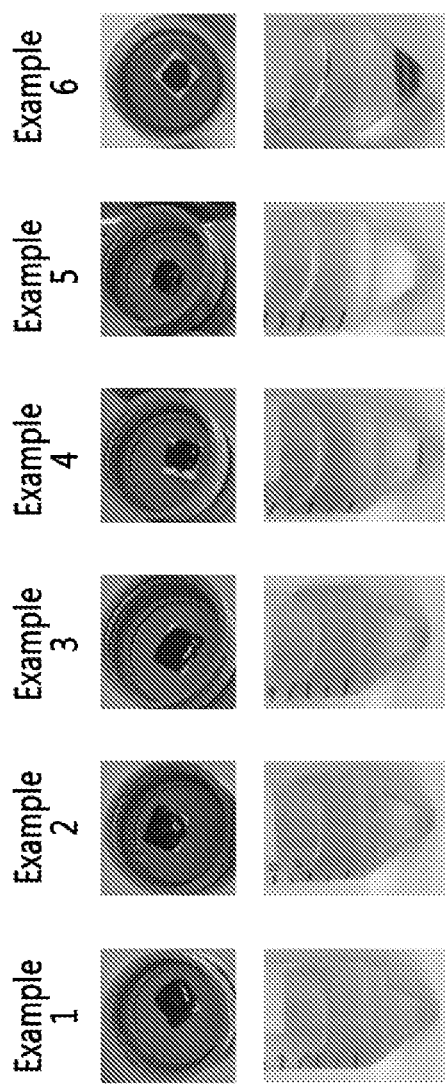
FIG. 5 is a photographic image showing blood coagulation property evaluation results of examples 1 to 6 and comparative examples 1 to 8.
Figure 5:
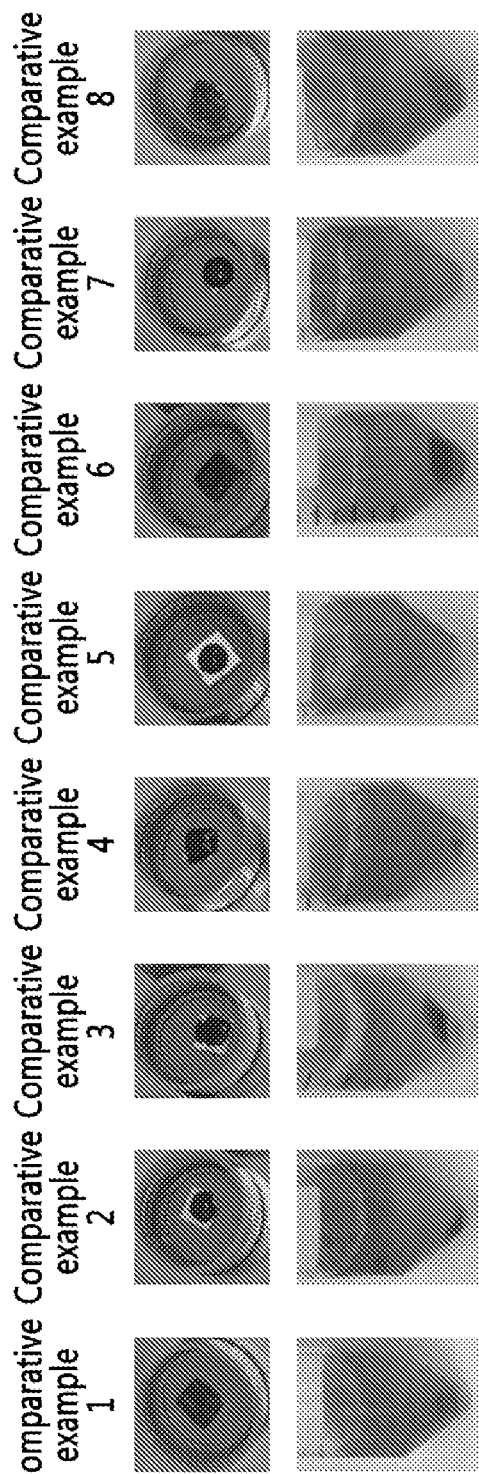

Referring to FIGS. 4 and 5, the medical fibrous structures of examples 1 to 6 had a smaller amount of blood that does not coagulate and is left as compared to exiting products of comparative examples 4 to 6, and thus had very low absorbance of the blood eluate as much as 0.1 or less and were found to have outstanding blood coagulation properties. In the case of comparative example 1, i.e., a nonwoven fabric consisting only of chitosan fibers, the blood coagulation properties markedly reduced. In the case of comparative examples 2 and 3 using sodium carboxymethyl cellulose, they showed blood coagulation properties that were equivalent to or better than commercial products of comparative examples 4 to 6, but their properties were remarkably poor as compared to examples 1 to 6 using calcium carboxymethyl cellulose.

Experimental Example: Blood Coagulation Rate

The blood coagulation properties as a function of coagulation time, namely, blood coagulation rate was evaluated using the medical fibrous structures prepared from examples 2, 4, and 5, comparative example 3, commercial products of comparative examples 4 and 6, and blood alone (comparative example 8).

The blood coagulation rate was evaluated by measuring absorbance of the blood eluate by the same method as described in "Experimental example: Evaluation of blood coagulation properties—coagulation time 10 minutes" except samples subjected to coagulation in a 37° C. incubator for the blood coagulation time of 1, 2, 3, 5 and 10 minutes were used. In the case of comparative example 8, absorbance was measured using blood alone without any hemostatic dressing by the same method as above. Its evaluated results are shown in the following FIG. 6.

Figure 6:
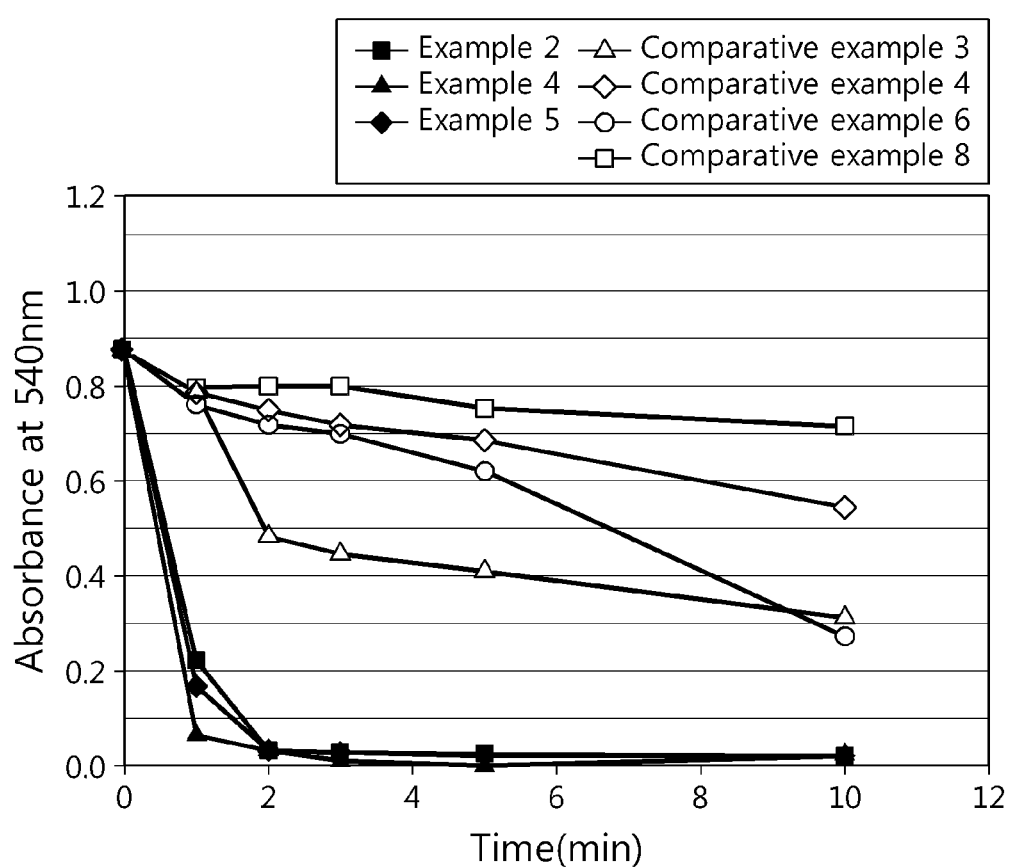
FIG. 6 is a graph showing evaluation of blood coagulation properties as a function of coagulation time for examples 2, 4, 5 and comparative examples 3, 4, 6, 8.

Referring to FIG. 6, in the case of examples 2, 4, and 5 including chitosan fibers or chitosan powder and calcium carboxymethyl cellulose, absorbance was found as being 0.3 or less even within 5 minutes, and further, absorbance was found as being 0.3 or less even in 1 minute after the start of coagulation, and thus it was identified that coagulation was almost completed within 1 minute.

In the case of commercial products of comparative example 4 and 6, absorbance was found as being 0.4 or more even in 5 minutes after the start of coagulation, showing a slow coagulation rate. In the case of comparative example 3 using 50 parts by weight of sodium carboxymethyl cellulose fibers, the blood coagulation rate was found relatively fast as compared to commercial products of comparative examples 4 and 6, while the blood coagulation rate was remarkably low as compared to example 2 using 50 parts by weight of calcium carboxymethyl cellulose fibers, and absorbance was still 0.4 or more after five minutes passed.

Experimental Example: Blood Absorption Rate

The blood absorption rate was evaluated using the medical fibrous structures of examples 2, 4, 5, and 6 prepared from 50 parts by weight of calcium carboxymethyl cellulose fibers and 50 parts by weight of chitosan fibers (or powder), the nonwoven fabric prepared in comparative example 3, and current commercial hemostatic dressing products of comparative examples 4 to 6.

The blood absorption rate is evaluated by measuring the time required for 100□ of blood to be completely absorbed by a nonwoven fabric of dimensions 1 cm×1 cm (width×length) after the blood was dripped into the nonwoven fabric, and from this, it was intended to evaluate suitability as hemostatic dressings.

The blood absorption rate results and photographic images before and after blood absorption are shown in the following FIG. 7. The photographic image after absorption is a photographic image after blood was dripped and completely absorbed. In the case of comparative examples 3 and 5, blood was not absorbed even after 10 minutes, so the photographic image is one after 10 minutes passed.

Figure 7:
FIG. 7 is a blood absorption rate results and photographic images before and after blood absorption.
Figure 7:
Figure 7:
Figure 7:
Figure 7:
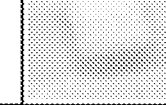
Figure 7:
Figure 7:
Figure 7:
Figure 7:
Figure 7:
Figure 7:
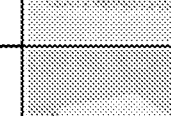
Figure 7:
Figure 7:
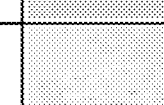
Figure 7:
Figure 7:
Figure 7:

As shown in FIG. 7, blood was absorbed by the medical fibrous structures according to examples using calcium carboxymethyl cellulose fibers as soon as the blood was dripped, while in the comparative example 3 using sodium carboxymethyl cellulose, blood was not completely absorbed even in 10 minutes after the blood was dripped.

What is claimed is:
1. A medical fibrous structure comprising:
   calcium carboxymethyl cellulose fiber; and
   a chitosan compound fiber,
   wherein a weight ratio of the calcium carboxymethyl cellulose fiber and the chitosan compound fiber is from 70:30 to 30:70,
   wherein a calcium content in the calcium carboxymethyl cellulose fiber is 2 to 12 wt % per a total weight of the calcium carboxymethyl cellulose fiber,
   wherein the medical fibrous structure has absorbance of 0.30 or less as a blood coagulation property when measured at following conditions:
   dripping 100 µl of a mixed solution of blood and an anticoagulant that is sodium citrate of 3.8 w/v % at a volume ratio of 9:1 into the medical fibrous structure of dimensions 1 cm×1 cm,
   inducing coagulation in a 37° C. incubator for 10 minutes with an addition of 10 µl of 0.2M $CaCl_2$ aqueous solution, eluting blood that does not participate in the coagulation of the blood in the mixed solution in 12.5 mL of distilled water, determining absorbance [AB] of 200 µl of the eluate at 540 nm wavelength, and absorbance [AW] of 200 µl of distilled water at 540 nm wavelength, and calculating the absorbance as the blood coagulation property by a following equation:

> the absorbance as the blood coagulation property=the absorbance of blood eluate [AB]− the absorbance of distilled water [AW].

2. The medical fibrous structure according to claim 1, wherein the medical fibrous structure includes at least one of a nonwoven fabric, a woven fabric, a knitted fabric, and a microfibril structure.

3. The medical fibrous structure according to claim 1, wherein the medical fibrous structure is at least one of a nonwoven fabric, a woven fabric, and a knitted fabric including calcium carboxymethyl cellulose fibers and chitosan compound fibers.

4. The medical fibrous structure according to claim 1, wherein the medical fibrous structure comprises a substrate including fibers formed of at least one of calcium carboxymethyl cellulose and a chitosan compound; and a fiber layer disposed on at least one of at least one surface of the substrate and an inside of the substrate, wherein the fiber layer includes fibers formed of at least one of calcium carboxymethyl cellulose and a chitosan compound, and the substrate is a nonwoven fabric, a woven fabric, or a knitted fabric.

5. The medical fibrous structure according to claim 1, wherein the medical fibrous structure is a microfibril structure including calcium carboxymethyl cellulose microfibrils and chitosan compound microfibrils.

6. The medical fibrous structure according to claim 5, wherein the chitosan compound is water-soluble chitosan.

7. A medical fibrous structure comprising:
calcium carboxymethyl cellulose fiber and chitosan compound powder,
wherein a weight ratio of the calcium carboxymethyl cellulose fiber and the chitosan compound power is from 70:30 to 30:70,
wherein a calcium content in the calcium carboxymethyl cellulose fiber is 2 to 12 wt % per a total weight of the calcium carboxymethyl cellulose fiber,
wherein the medical fibrous structure has absorbance of 0.30 or less as a blood coagulation property when measured at following conditions:

dripping 100 µl of a mixed solution of blood and an anticoagulant that is sodium citrate of 3.8 w/v % at a volume ratio of 9:1 into the medical fibrous structure of dimensions 1 cm×1 cm;

inducing coagulation in a 37° C. incubator for 10 minutes with an addition of 10 µl of 0.2M CaCl2 aqueous solution;

eluting blood that does not participate in the coagulation of the blood in the mixed solution in 12.5 mL of distilled water;

determining absorbance [AB] of 200 µl of the eluate at 540 nm wavelength, and absorbance [AW] of 200 µl of distilled water at 540 nm wavelength; and calculating the absorbance as the blood coagulation property by a following equation:

> the absorbance as the blood coagulation property=the absorbance of blood eluate [AB]− the absorbance of distilled water [AW].

8. The medical fibrous structure according to claim 7, wherein the powder form is powder having an average particle diameter of from 1 µm to 1,000 µm.

9. The medical fibrous structure according to claim 7, wherein the medical fibrous structure comprises:
a substrate including fibers formed of calcium carboxymethyl cellulose; and
a coating layer disposed on at least one surface of the substrate and an inside of the substrate,
wherein the coating layer includes powder formed of a chitosan compound, and
wherein the substrate is a nonwoven fabric, a woven fabric, or a knitted fabric.

10. The medical fibrous structure according to claim 9, wherein the coating layer is formed as a patterned layer on at least one surface of the nonwoven fabric.

11. The medical fibrous structure according to claim 7, wherein the chitosan compound is water-soluble chitosan.

12. The medical fibrous structure according to any of claims 1, 2, and 3 to 11, further comprising:
a structure reinforcement on at least one of at least one surface and an inside of the medical fibrous structure.

\* \* \* \* \*